United States Patent [19]
Jones

[11] Patent Number: 5,197,340
[45] Date of Patent: Mar. 30, 1993

[54] METHOD AND APPARATUS FOR SAMPLING LIQUID

[76] Inventor: Richard W. Jones, Warren Jones Engineering Limited, 120-124 Churchill Rd., Bicester, Oxfordshire OX6 7XD, United Kingdom

[21] Appl. No.: 687,886
[22] PCT Filed: Oct. 2, 1990
[86] PCT No.: PCT/GB90/01509
  § 371 Date: Jul. 31, 1991
  § 102(e) Date: Jul. 31, 1991
[87] PCT Pub. No.: WO91/05234
  PCT Pub. Date: Apr. 18, 1991

[30] Foreign Application Priority Data

Oct. 2, 1989 [GB] United Kingdom ............ 8922118
Mar. 30, 1990 [GB] United Kingdom ............ 9007189

[51] Int. Cl.$^5$ .................................. G01N 1/14
[52] U.S. Cl. ..................................... 73/864.35
[58] Field of Search ............ 73/863.1–863.3, 73/863.84, 863.85, 864.34, 864.35

[56] References Cited

U.S. PATENT DOCUMENTS

| | | | |
|---|---|---|---|
| 3,209,598 | 10/1965 | Anderson et al. | 73/864.35 |
| 3,587,670 | 6/1971 | Brailsford | 73/864.35 |
| 3,589,197 | 6/1971 | Brooks, Sr. . | |
| 3,691,844 | 9/1972 | Moore . | |
| 3,901,087 | 8/1975 | Hannes Fabritius . | |
| 4,037,472 | 7/1977 | Gates | 73/864.35 |
| 4,163,392 | 8/1979 | Fleenor et al. | 73/864.35 |
| 4,418,581 | 12/1983 | Jones . | |

OTHER PUBLICATIONS

Patent Abstracts of Japan, vol. 10, No. 327, P513, abstract of JP 61-133835, publ. Jun. 21, 1986 (Fuji Electric Co., Ltd.).

Primary Examiner—Robert Raevis
Attorney, Agent, or Firm—Davis, Bujold & Streck

[57] ABSTRACT

A method of, and apparatus for, liquid sampling by way of a self contained unit for: 1) the periodical coupling of a pressurizable sample chamber to a source of sub-atmospheric pressure to cause a bulk sample of liquid for sampling to be drawn into the chamber from a body of liquid by a first passasge; 2) the retention of a sample volume thereof in the chamber while allowing surplus liquid from the bulk sample to drain from the chamber by way of the first passage; and 3) allowing the retained sample volume to pass out the chamber by way of a second passage under the control of a delivery valve wherein the periodical coupling of the sample chamber to a source of sub-atmospheric pressure is undertaken by way of a valve system comprising first and second flexible tubes, the first flexible tube linking a source of air at super-atmospheric pressure to the chamber and the second tube linking a source of air at sub-atmospheric pressure to the chamber; and a first clamping device in the form of a cam which can, depending on the disposition of the cam, alternately: 1) distort the first tube to prevent the chamber from communicating with the sub-atmospheric source while allowing the chamber to communicate with the super-atmospheric source by way of the second tube; and ii) distort the first tube to prevent the chamber from communicating with the super-atmospheric source while allowing the chamber to communicate with the sub-atmospheric source by way of the second tube.

6 Claims, 4 Drawing Sheets

METHOD AND APPARATUS FOR SAMPLING LIQUID

This invention relates to a method and to apparatus for sampling liquid. It is particularly concerned with the sampling of waste waters so as to obtain a representative portion of liquid from which its average composition can be determined.

When sampling a flowing liquid, such as waste waters from a drain, a common requirement is to establish its average composition over a specific period (such as twenty four hours). This is normally achieved by aggregating a set of individual sub-samples taken with sufficient frequency to include all the effect of changes in composition of the flow over the period of the sample. Individual sub-samples can either be aggregated in a single container to provide a bulk sample giving a gross average or alternatively each sub-sample can be passed into a separate container in a sequence of such to store samples of the flow from hour to hour.

The more frequent the taking of the samples the more representative the eventual aggregated sample will be. The frequency of sampling may be at regular time intervals or at time intervals whose length are in inverse proportion to a rate of flow of the sampled liquid (such sampling is termed 'flow proportional sampling').

When sampling waste waters it is important to include solid wastes carried by the waters so that the, or each, sample is representative of the material flowing or conveyed at the time of sampling. Consequently an effective sampling system needs to be able to provide for the passage of solid waste components into a sample container.

According to a first aspect of the present invention there is provided a method of liquid sampling by way of a self contained unit comprising the steps of:
1. periodically coupling a pressurisible sample chamber to a source of sub-atmospheric pressure to cause a bulk sample of liquid for sampling to be drawn into the chamber from a body of liquid by way of a first passage;
2. retaining a sample volume thereof in the chamber while allowing surplus liquid from the bulk sample to drain from the chamber by way of the first passage; and
3. allowing the retained sample volume to pass out of the chamber by way of a second passage under the control of a delivery valve characterised in that:
   the method of periodically coupling the sample chamber to the source of sub-atmospheric pressure is undertaken by way of a valve system comprising first and second flexible tubes, the first flexible tube linking a source of air at atmospheric pressure to the chamber and the second tube linking the source of air at sub-atmospheric pressure to the chamber: and a first clamping device in the form of a first cam which can, depending on the disposition of the first cam, alternately:
   i) distort the first tube to prevent the chamber communicating with the sub-atmospheric source while allowing the chamber to communicate with the atmospheric source by way of the second tube;
   ii) distort the first tube to prevent the chamber communicating with the atmospheric source while allowing the chamber to communicate with the sub-atmospheric source by way of the second tube.

According to a first preferred version of the first aspect of the present invention the step of allowing at least a part of sample volume hitherto retained in the sample chamber to pass out of the chamber by the second passage is characterised by the use of a flexible duct and is undertaken by way of a second clamping device operable between open and closed positions by way of a second cam so that:
   i) in the closed position the second clamping device distorts the outlet duct to prevent the passage of sample volume out of the chamber by way of the flexible duct; and
   ii) in the open position the second clamping device enables the passage of sample volume out of the chamber by way of the flexible duct.

Preferably the first and second clamping devices are powered by a common prime mover.

According to a second preferred version of the first aspect of the present invention or the first preferred version thereof the first clamping device is characterised by being in the form of a cam and an anvil, the cam being located eccentrically and rotatable relative to the anvil to leave a sequence of working clearances therebetween, each flexible duct being located in a working clearance.

According to a third preferred version of the first aspect of the present invention or any preceding preferred version thereof the second clamping device takes the form of a pivoted clamp having jaws acting on the outlet duct which jaws are displacable between the open and closed positions by the second cam.

According to a fourth preferred version of the first aspect of the present invention or any preceding preferred version thereof the action of the prime mover on the second cam to close the outlet duct occurs before the combined actions of the same prime mover on the first cam to distort the first tube to prevent the chamber communicating with the atmospheric source while allowing the chamber to communicate with the sub-atmospheric source by way of the second tube.

According to a fifth preferred version of the first aspect of the present invention the method is characterised by the provision of a source of super-atmospheric pressure which can communicate with the pressurisable sample chamber by way of a third flexible tube; the cam of the first clamping device serving, at a particular disposition:
   i) to distort the first and second tubes to prevent the chamber communicating with the atmospheric and sub-atmospheric source while allowing the chamber to communicate with the super-atmospheric source by way of the third tube and similarly to claim 1;
   ii) to distort the first and third tubes to prevent the chamber communicating with the atmospheric and super-atmospheric source while allowing the chamber to communicate with the sub-atmospheric source by way of the second tube;
   iii) to distort the second and third tubes to prevent the chamber communicating with the sub-atmospheric and super-atmospheric source while allowing the chamber to communicate with the atmospheric source by way of the first tube.

According to a second aspect of the present invention there is provided apparatus for liquid sampling comprises a housing incorporating a pressurisible sample chamber and characterised by:

1. a sample inlet and a sample outlet at the lower end of the chamber and a pressure control port at the upper end;
2. an air displacer, such as a compressor, adapted to generate a relatively low, typically sub-atmospheric, pressure in a vacuum duct and to generate a relatively high, typically super-atmospheric pressure, in a pressure duct;
3. a valve system comprises or includes a first clamping device in the form of a cam and two anvils across each pair of anvils a pair of flexible tubes is located, one pair of tubes communicate between the pressure control port and the vacuum duct and between the pressure control port and the atmosphere, the other pair of tubes communicate between the vacuum duct and the control port and between the pressure duct and the atmosphere so that:
   i) the vacuum duct can be made to communicate in a first mode with the chamber by way of the pressure control port and in a second mode via an air inlet duct to atmosphere;
   ii) the pressure duct can be made to communicate in a third mode with the chamber by way of the pressure control port and in a fourth mode via an air outlet duct with atmosphere; the valve system serving to provide, at the pressure control port:
      a) a vacuum action during the first mode;
      b) a pressure action during the third mode; and
      c) a substantially atmospheric venting action during the second and fourth modes.

According to a first preferred version of the second aspect of the present invention there is provided apparatus for liquid sampling according to the second aspect characterised in that the sample outlet comprises or includes a flexible duct and there is provided a delivery valve for regulating flow from the chamber through the sample outlet comprising a second clamping device operable between:
1. a closed position wherein the delivery valve serves to distort the flexible duct to prevent the passage of liquid from the chamber by way of the outlet duct; and
2. an open position wherein the delivery valve serves to enable the passage of liquid from the chamber by way of the outlet duct.

According to a second preferred version of the second aspect of the present invention apparatus according to the second aspect or the first preferred version thereof is characterised in that the first and second clamping devices are actuated by a common prime mover to enable the order of operating events to be readily related to one another so that the operation of the air displacer, the delivery valve and the control valve are adapted to perform a method in accordance with the first aspect of the present invention.

According to a third preferred version of the second aspect of the present invention of any preceding preferred version thereof apparatus for liquid sampling is characterised in that the first clamping device includes at least one motor driven cam and an anvil defining a workspace clearance therebetween so that:
1. in a first position workspace clearance is reduced to a minimum so as to cause a duct in the array thereof to be distorted so that communication between the pressure duct and the air inlet is interrupted;
2. in a second position workspace clearance is reduced to a minimum as to cause a duct in the array thereof to be distorted so that communication between the vacuum duct and the air outlet is interrupted; and
3. in a third position workspace clearance approaches or is at a maximum so that distortion of at least one duct in the array thereof is minimised to facilitate flow along the duct.

According to a fourth preferred version of the present invention the apparatus for liquid sampling is characterised by a control system regulating operation of the valve system and providing for either the first or second modes or for the third and fourth modes to be established.

According to a fifth preferred version of the present invention the apparatus for liquid sampling according to the second aspect is characterised by adjustment means to enable vertical separation of the inlet port and the outlet port to be variable to vary the size of the retained sample.

According to a sixth preferred version of the second aspect of the present invention or any preceding preferred version thereof apparatus for liquid sampling is characterised by at least a portion of the chamber being of transparent material and means are provided for propagating a beam of light or other radiation into the chamber and for detecting such a beam or characteristics thereof such as intensity at least when the beam or characteristics thereof are subject to a change such as is caused by a rising free liquid surface within the chamber.

EXEMPLARY EMBODIMENT

An exemplary embodiment of the invention will now be described with reference to the accompanying drawings of a portable sampler broadly comprising a sample taking module, a sample distributing module and a sample carrier. The drawings are made up of.

Items appearing in more than one figure are identified by the same reference throughout.

Figure 1:
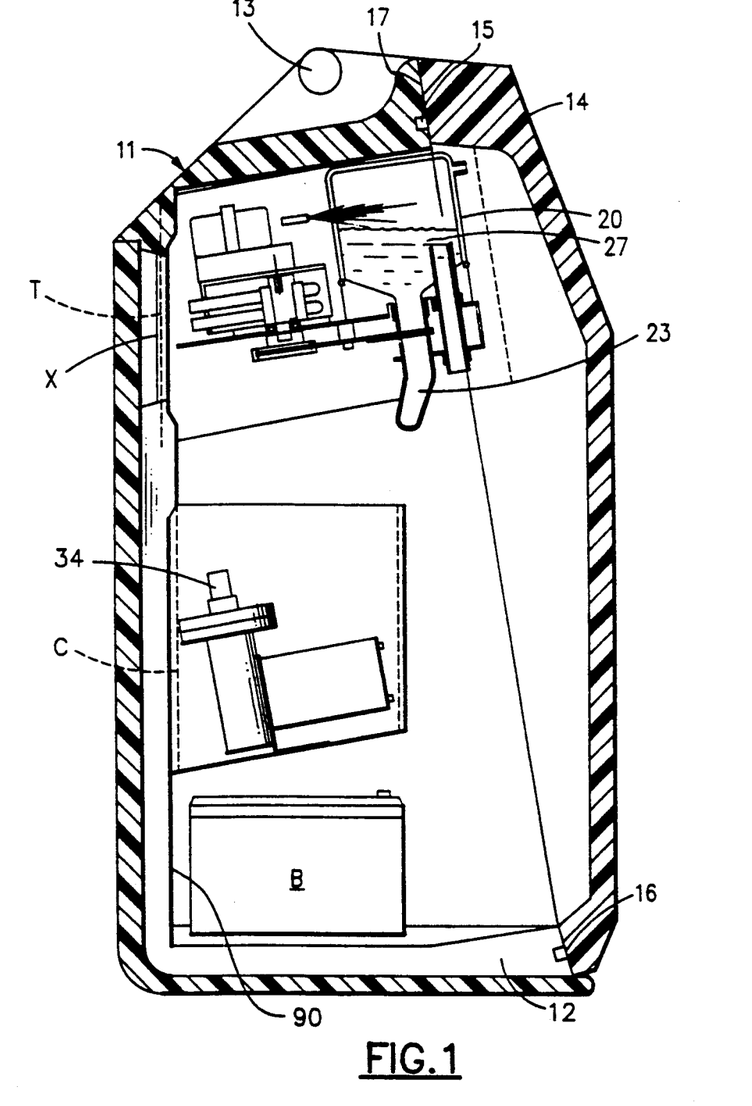
FIG. 1 which is a sectional elevation.

FIG. 1 shows a sampler housing 11 made up of a body 12, with an integral carrying handle 13, and a hinged door 14. Both the body 12 and the door 14 are of double skinned foam filled plastics material. A resilient seal 15 is positioned in slot 16 in front flange 17 of the body to provide for a weathertight seal between body and door when closed together and retained in place by over centre clips (not shown).

The housing 11 serves to retain a number of modular assemblies which can be readily accessed and, where necessary, removed. Within the housing from the top down these include: a sample taking module T; a compressor/motor assembly C; and a battery B. In addition there are miscellaneous items providing service and other support for the modules which will be touched on hereafter.

SAMPLE TAKING MODULE T

Figure 2:
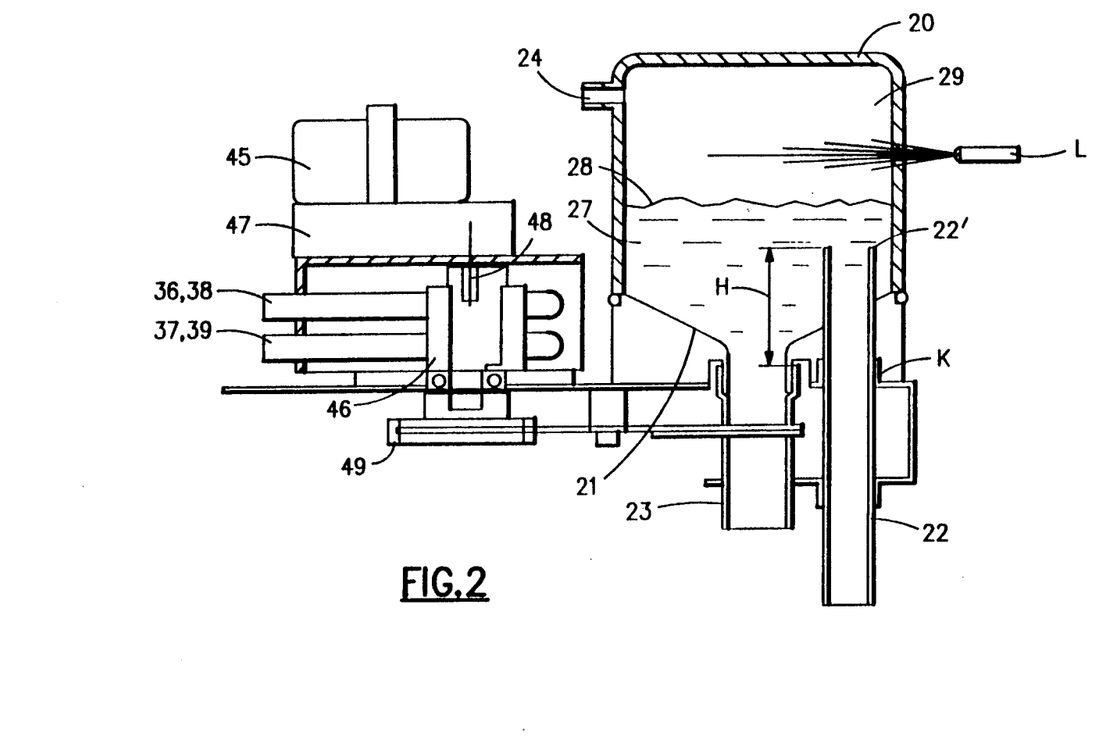
FIG. 2 which is an enlargement of a sample taking module located in the upper part of FIG. 1.
Figure 3:
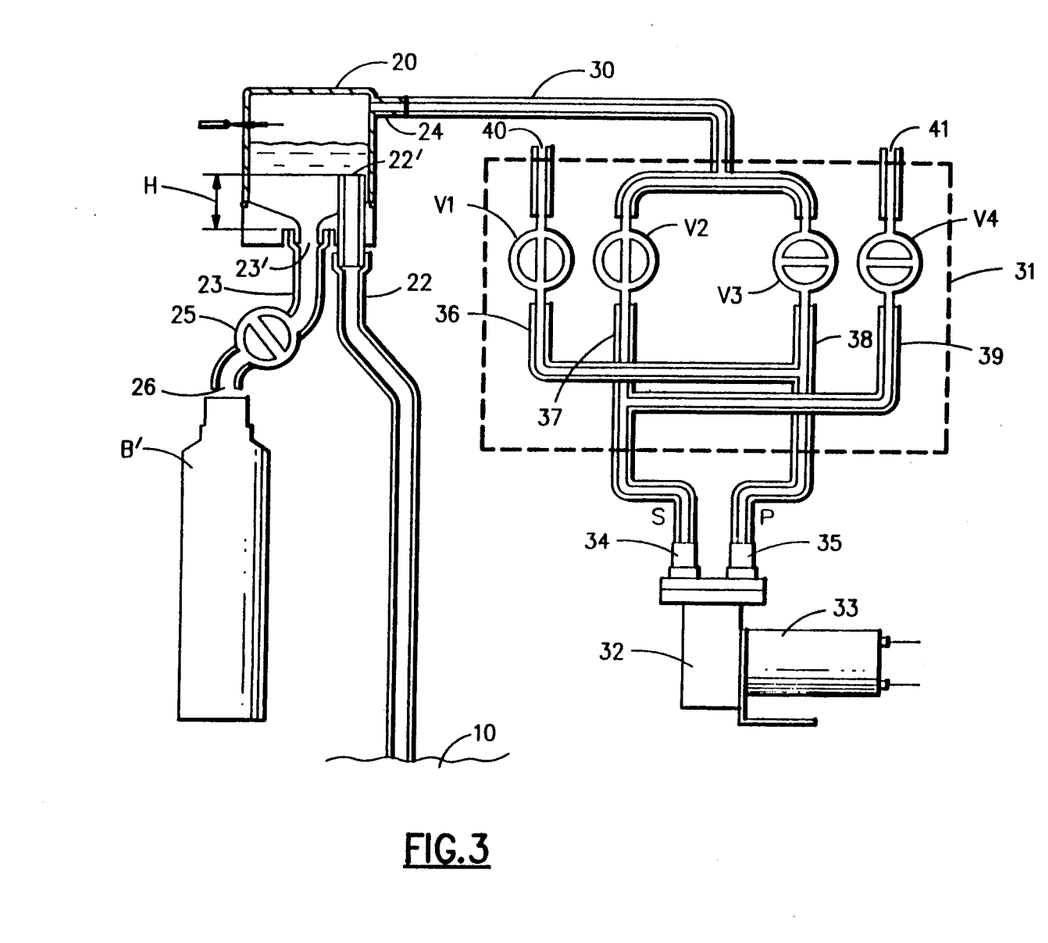
FIG. 3 which is a schematic diagram of the valve and ducting arrangements of the sampler.
Figure 4A:
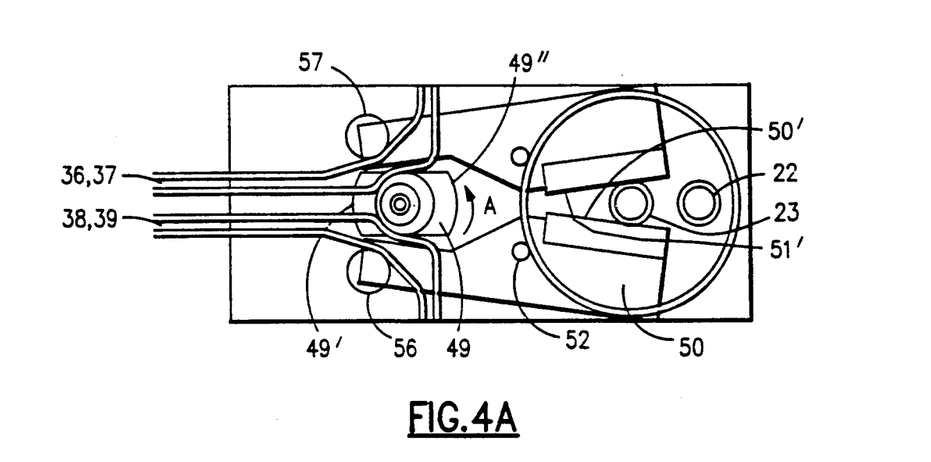
FIGS. 4A to 4C which are sectional views on section IV—IV of FIG. 2 showing various operating positions of valves therein.
Figure 4B:
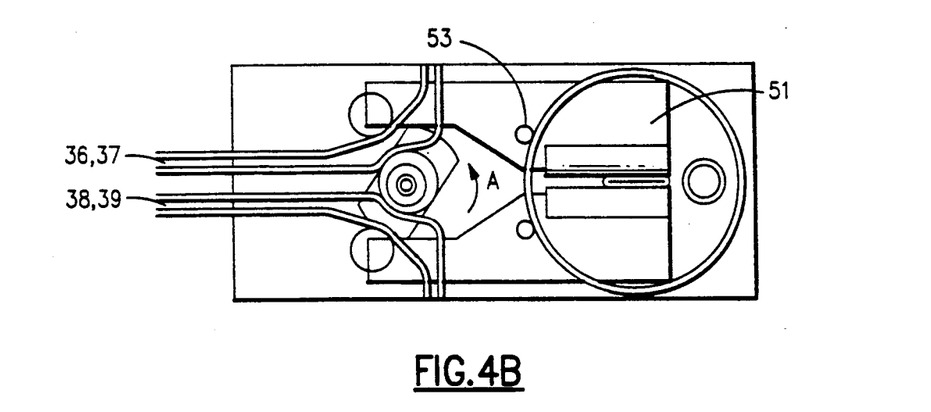
Figure 4C:
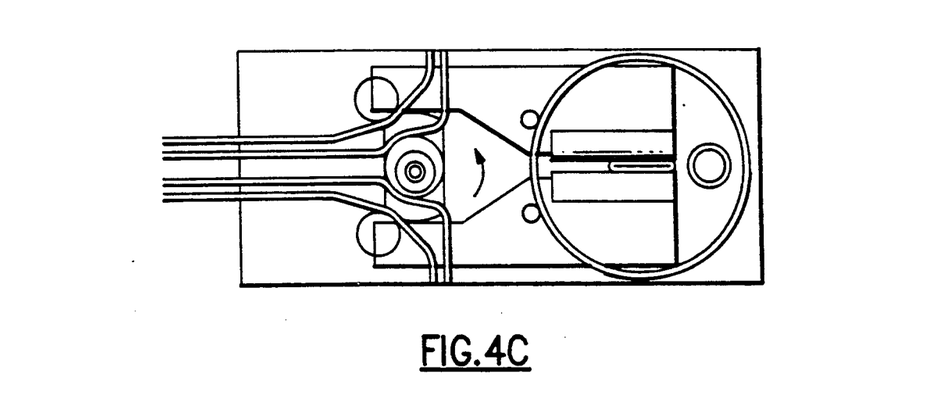

In addition to the general view in FIG. 1 the significant features of the sample taking module T are shown in FIG. 2 while FIG. 3 shows the relationship between the various flow paths in the module and FIG. 4 shows the relative positions of various components of the sample taking module whilst in operation.

Working chamber 20 has a conical lower end 21 through which passes a flexible sampling tube 22. A sample delivery duct 23 projects downwardly from the bottom of the working chamber 20. Entry 22' of the sampling tube 22 is located at a height H above the bottom of the chamber 20. The mounting of the tube 22 relative to the chamber 20 is by way of a slidable fit sleeve K so as to enable the height H, and so the volume of the sample which can be provided from the chamber 20, to be varied. Material for sampling is drawn into tube 22 by applying a sub-atmospheric pressure to the interior of the chamber 20, and so to the tube 22, by way of port 24.

To clarify the relationships between the various modules and hardware of the sampler the flow arrangements will now be described with reference to FIGS. 3 and 4.

FIG. 3 shows the working chamber 20, sampling tube 22 and delivery duct 23. The sampling tube 22 extends outwardly of the housing 11 to an outer end remote from the chamber 20. The outer end is adapted for location in a water flow which is to be sampled. The delivery duct 23 extends downwardly by way of a control valve 25 to outlet end 26 which can be located above a sample bottle B'.

Reverting now to FIG. 2 the working chamber 20 contains a volume 27 of sampled liquid with a free surface 28 between the volume 27 and air volume 29. The wall of the working chamber 20 are transparent and a level sensor L is provided to detect for the presence, or absence, of free surface 28 or for the presence or absence of liquid in the course of a working cycle.

The pressure in volume 29 is regulated by way of the port 24 which is linked by pipe 30 (FIG. 3) to a pressure control manifold 31.

Air compressor 32 powered by electric motor 33 has outlets 34, 35 providing, respectively, sub- and super-atmospheric pressure to the manifold 31. The appropriate pressure is applied to, or isolated from, the pipe 30 by way of an array of valves V1, V2, V3, V4 located, respectively, in branches 36, 37, 38, 39. In particular valve V1 and V4 enable the manifold 31 to be vented to atmosphere by way of, respectively, outlets 40, 41. In this way pressure in the manifold can be restored to atmospheric when the compressor 32 is not running.

The practical arrangement and operation of the control valve 25 and of the valves V1 to V4 are now described with particular reference to FIGS. 2 and 4. All the valves (25 and V1, V2, V3, V4) are powered by way of a stepper motor 45 driving an eccentric shaft 46 by way of a gearbox 47 with output shaft 48.

Considering firstly valve 25. Eccentric shaft 46 drives a pinch cam 49 which (see particularly FIG. 4) acts to open and close pinch arms 50, 51 mounted for pivoting about, respectively, pivots 52, 53. The pinch cam 49 and arms 50, 51 together form the valve 25 shown in FIG. 3. The cam 49 can be oscillated in the direction of arrow A or in the opposite direction and has a suitably shaped actuating edge 49' and dwell surface 49". The pivot arms 50, 51 have pinch faces 50', 51' which serve to pinch sample outlet tube 23 so that in the course of an operating cycle flow along the tube 23 can be allowed or prevented. FIG. 4B and 4C show the tube 23 pinched shut, FIG. 4A shows the tube 23 fully open.

Valves V1 to V4 are embodied an eccentric 46 which interact with rigid columns (anvils) 56, 57 to provide for the opening or closing of one or other of flexible branches 36 to 39 as required during a sampling cycle.

In FIGS. 4A-C only branches 36, 38 are shown together with valves V1, V2 (made up of eccentric 46 and, respectively, columns rollers 56, 57). Branches 37, 39 are located behind, respectively, branches 36, 38 as shown in FIGS. 4A-C.

FIGS. 4A, 4B, 4C shows the relative position of the parts during one half of the cycle of operation of output shaft 48. Rotation of the shaft 48 in the opposite direction to arrow A in FIG. 4A serves to pinch tubes 38, 39 instead of tubes 36, 37 and this action serves to form the other half of the operating cycle of the shaft 48.

FIG. 4A shows the situation at the start of the cycle with tube 23 and branches 36, 37 all fully open and pinch cam 49 turning in direction of arrow A.

FIG. 4B shows the position about 45 degrees later with the tube 23 pinched shut and branches 36, 37 still open.

FIG. 4C shows the position about 90 degrees after that shown in FIG. 4A with tube 23 still closed and tube 39 fully open.

The following table shows the status of the valves 25 and V1 to V4 for the positions shown in FIG. 4.

| Valve (governing | Valve 25 Tube 23 | V1 Branch 36 | V2 Branch 37 | V3 Branch 38 | V4 Branch 39) |
| --- | --- | --- | --- | --- | --- |
| FIG. 4A | open | open | open | open | open |
| FIG. 4B | closed | partially open | partially open | open | open |
| FIG. 4C | closed | substantially closed | substantially closed | open | open |

The downstream end 26 of the flexible outlet pipe 23 is located over an inlet to a sample bottle B. This bottle is periodically removed to enable the collected liquid to be analysed in a known manner depending on the working requirements. In view of the simplicity of this arrangement no further description is made of the collection arrangement. The subject of applicants co-pending application is a distribution system whereby a number of samples can be distributed and retained in each of a number of bottles in a predetermined order.

The present description refers to a transportable sampler. However the sample taking module can be used as an independent unit outwith the module in a situation where the question of portability does not arise.

MISCELLANEOUS ITEMS

FIG. 1 shows a void 90 containing battery B for powering the sampler motors and motor/compressor module C.

In addition at the top of the casing 11 is located a control unit X including a printed circuit board, keyboard and a microprocessor programmable to regulate the operation of the sample taking module and where necessary any sample distribution module.

The location of the various components within the housing 11 provides for an efficient and compact assembly which is readily portable. By locating the heavier components, such as the battery B and motor/compressor module C, at the bottom of the sampler a stable structure with a centre of gravity as low as is practicable is achieved.

I claim:

1. An apparatus for liquid sampling comprising a housing provided with a sample inlet branch and a sample outlet branch characterized by:
   1) a pressurizible sample chamber (20) communicating with the inlet and the outlet branches;
   2) an air displacer (32) adapted to generate
      a) a sub-atmospheric pressure in a vacuum duct (34); and
      b) a super-atmospheric pressure in a pressure duct (35);
   3) an array of four branches (36, 37, 38, 39) made up of:
      a) a first branch (36) linking the pressure duct (35) to an atmospheric outlet (40) and incorporating a first valve (V1);
      b) a second branch (37) linking the vacuum duct (34) to the sample chamber (20) by way of pressure control port (24) and incorporating a second valve (V2);
      c) a third branch (38) linking the pressure duct (35) to the sample chamber (20) by way of pressure said control port (24) and incorporating a third valve (V3); and
      d) a fourth branch (39) linking the vacuum duct (34) to an atmosphoric inlet (41) and incorporating a fourth valve (V4);
   4) the first valve (V1) and the second valve (V2) comprising a first cam (46), a first anvil (57) and flexible sections of each of the first branch (36) and of the second branch (37) passing between the first cam (46) and the first anvil (57); the third valve (V3) and the fourth valve (V4) comprising the first cam (46) and a second anvil (56) and flexible sections of each of the third branch (38) and of the fourth branch (39) passing between the first cam (46) and the second anvil (56); the first cam (46) being operable to deform and release from deformation the flexible sections of pairs of the first to the fourth branches (36–39) so that:
      a) in a first operating mode, the first valve (V1) and the second valve (V2) are each open, and the third valve (V3) and the fourth valve (V4) are each closed to provide for the pressure duct (35) to vent to atmosphere by way of the first branch (36) and the outlet (40) and for the vacuum duct (34) to communicate with the sample chamber (20) by way of the second branch (37);
      b) in a second operating mode, the first valve (V1), the second valve (V2), the third valve (V3) and the fourth valve (V4) are all open to allow the vacuum duct (34) to be open to atmosphere by way of the fourth branch (39), the pressure duct (35) to be open to atmosphere by way of the first branch (36) and the sample chamber (20) to vent to atmosphere;
      c) in a third operating mode, the third valve (V3) and the fourth valve (V4) are each open and the first valve (V1) and second valve (V2) are each closed, to provide for the vacuum duct (34) to be vented to atmosphere by way of the fourth branch (39) and the inlet (41) and the pressure duct (35) to communicate with the sample chamber (20) by way of the third branch (38); and
      d) in a fourth operating mode, the first valve (V1), the second valve (V2), the third valve (V3) and the fourth valve (V4) are all open to provide for the vacuum duct (34) to open to atmosphere by way of the fourth branch (39), the pressure duct (35) to be open to atmosphere by way of the first branch (36) and the sample chamber (20) to vent to atmosphere;
   5) the sample outlet branch (23) including a delivery valve (25), disposed in the outlet branch (23), for regulating liquid flow there along from the sample chamber (20); the delivery valve (25) comprising a clamping device made up of a pinch cam (49) driving a clamp (50, 51), and a flexible section of the outlet branch (23) extending through the clamp (50, 51); the delivery valve (25) being operable, in relation to a state of the first, the second, the third and the fourth valves (V1 to V4), between:
      i) a closed position in which the clamp (50, 51) serves to clamp the flexible section of the outlet branch (23) to inhibit the flow of liquid along the outlet branch (23) from the sample chamber (20) to a sample collection device; and
      ii) an open position in which the clamp (50, 51) does not inhibit the passage of liquid through the outlet branch (23) to the sample collection device; and
   6) a prime mover (45) coupled to drive both the first cam (46) and the pinch cam (49) providing for operation of the first, the second, the third and the fourth valves (V1, V2, V3, V4) and the delivery valve (25) to be mechanically related.

2. An apparatus for liquid sampling as claimed in claim 1 wherein the apparatus is a vertical separation apparatus with at least one of an inlet end (22′) of the inlet branch (22) and an outlet end (23′) of the outlet branch (23) being vertically adjustable to vary the size of a retained sample (27) in the sample chamber (20).

3. An apparatus for liquid sampling as claimed in claim 2 wherein at least a portion of the sample chamber (20) is made of a transparent material and a light source (L) is provided for propagating a beam of light into the sample chamber (20) and for detecting at least one of the beam and characteristics of the beam.

4. An apparatus for liquid sampling as claimed in claim 1 wherein at least a portion of the sample chamber (20) is made of a transparent material and detection means (L) is provided for propagating a beam into the sample chamber (20) for detecting a presence of liquid in the sample chamber (20).

5. An apparatus for liquid sampling comprising a housing provided with a sample inlet branch and a sample outlet branch characterized by:
   1) a pressurizible sample chamber (20) communicating with the inlet and the outlet branches;
   2) an air displacer (32) adapted to generate a relatively low, sub-atmospheric, pressure in a vacuum duct (34);
   3) an array of two branches (37, 39) made up of:
      a) a suction branch (37) linking the vacuum duct (34) to the sample chamber (20) by way of a pressure control port (24) and incorporating a suction valve (V2); and
      b) a venting branch (39) linking the vacuum duct (34) to an atmospheric inlet (41) and incorporating a vent valve (V4);
   4) the suction valve (V2) comprising a first cam (46), a first anvil (57) and a flexible section of the suction branch (37) passing between the first cam (46) and the first anvil (57); the vent valve (V4) comprising the first cam (46), a second anvil (56) and a flexible section of the venting branch (39) passing between the first cam (46) and the second anvil (56);

the first cam (46) being operable to provide for lobes on the first cam (46) to deform and release from deformation the flexible sections of the suction branch (37) and the vent branch (39) so that:

a) in a first operating mode, the suction valve (V2) is open and the vent valve (V4) closed to provide for the vacuum duct (34) to communicate with the sample chamber (20) by way of the suction branch (37);

b) in a second operating mode, the suction valve (V2) and the vent valve (V4) valve are both open to provide for the vacuum duct (34) to open to atmosphere by way of vent branch (39) and to provide for the sample chamber (20) to vent to atmosphere; and c) in a third operating mode, the vent valve (V4) is open and the suction valve (V2) closed to provide for the vacuum duct (34) to be vented to atmosphere by way of the vent branch (39);

5) the sample outlet branch (23) including a delivery valve (25) disposed in the outlet branch (23) for regulating liquid flow there along from the sample chamber (20) to a sample collection device; the delivery valve (25) comprising a clamping device made up of a pinch cam (49) driving a clamp (50, 51) and a flexible section of the outlet branch (23) extending through the clamp (50, 51); the delivery valve (25) being operable, in relation to a state of the suction valve (V2) and the vent valve (V4), between:

i) a closed position in which the clamp (50, 51) serves to clamp the flexible section of the outlet branch (23) to inhibit the flow of liquid along the outlet branch (23) from the sample chamber (20) to the sample collection device; and ii) an open position in which the clamp (50, 51) does not inhibit the passage of liquid through the outlet branch (23) to the sample collection device; and 6) a prime mover (45) coupled to drive both the first cam (46) and the pinch cam (49) providing for operation of the suction valve (V2), the vent valve (V4) and the delivery valve (25) to be mechanically related.

6. A method of operating a liquid sampling apparatus comprising the steps of:

providing a sampling apparatus comprising:

1) a housing provided with a pressurizible sample chamber (20), the sample chamber (20) communicating with an inlet duct and an outlet duct, the inlet duct (22) having a first end connected to an inlet (22') of the sample chamber (20), an opposite end of the sample inlet duct (22) communicating with a body of liquid to be sampled (10), and the sample chamber having a liquid level sensor (L) for detecting presence of a liquid sample in the sample chamber (20);

2) an air displacer (32) adapted to generate
a) a relatively low, sub-atmospheric, pressure in a vacuum duct (34); and
b) a relatively high, super-atmospheric, pressure in a pressure duct (35);

3) a sample outlet duct (23) having an outlet (23') adjacent a base of the sample chamber (20), the outlet duct (23) including a delivery valve (25) disposed in the outlet duct (23) for regulating liquid flow there along from the sample chamber (20) to a collection device; the delivery valve (25) comprising a clamping device made up of a double lobed cam (49) on a shaft (48) driving clamps (50,51) and a flexible section of the outlet duct (23) extending through the clamps (50, 51); the delivery valve (25) being operable between:

i) a closed position in which the clamps (50, 51) serve to clamp the flexible section of outlet duct (23) to inhibit the flow of liquid along the outlet duct (23) from the sample chamber (20) to the collection device; and ii) an open position in which the clamps (50, 51) do not inhibit the passage of liquid through the outlet duct (23) to the collection device;

4) an array of four pipe branches (36, 37, 38, 39) made up of:

a) a first branch (36) linking the pressure duct (35) to an atmospheric outlet (40) and incorporating a first valve (V1);

b) a second branch (37) linking the vacuum duct (34) to the sample chamber (20) by way of pressure control port (24) and incorporating a second valve (V2);

c) a third branch (38) linking the pressure duct (35) to the sample chamber (20) by way of the pressure control port (24) and incorporating a third valve (V3); and d) a fourth branch (39) linking the vacuum duct (34) to an atmospheric inlet (41) and incorporating a fourth valve (V4);

5) the first valve (V1) and the second valve (V2) comprising a single lobed cam (46) on the shaft (48), a first anvil (56) and flexible sections of each of the first branch (36) and of the second branch (37) passing between the single lobed cam (46) and the first anvil (56); the third valve (V3) and the fourth valve (V4) comprising the same lobed cam (46) and a second anvil (57) and flexible sections of each of the third branch (38) and of the fourth branch (39) passing between the single lobed cam (46) and the second anvil (57); both said cams (46, 49) being operated by the same shaft (48) to provide for the single lobed cam (46) to deform and release from deformation the flexible sections of pairs of the first to the fourth branches (36–39) in unison with the clamps (50,51) so that:

a) in a first operating mode, the first valve (V1) and the second valve (V2) are each closed and the third valve (V3) and the fourth valve (V4) are each open to provide for the vacuum duct (34) to vent to atmosphere by way of the fourth branch (39) and the inlet (41) and for the pressure duct (34) to communicate with the sample chamber (20) by way of the third branch (38) while the clamps (50, 51) inhibit the passage of liquid through the delivery duct (25);

b) in a second operating mode, the third valve (V3) and the fourth valve (V4) are each closed and the first valve (V1) and the second valve (V2) are each open to provide for the pressure duct (35) to be vented to atmosphere by way of the first branch (36) and the outlet (40) and the vacuum duct (34) to communicate with the sample chamber (20) by way of the second branch (37) while the clamps (50, 51) inhibit the passage of liquid through the delivery duct (25); and c) in a third operating mode, the first valve (V1), the second valve (V2), the third valve (V3) and the fourth valve (V4) are all open to provide for the vacuum duct (34) to open to atmosphere by way of the fourth branch (39), the pressure duct (35) to be open to atmosphere by way of the first branch (36) and the sample chamber (20) to vent to atmosphere while the clamps (50, 51) inhibit the passage through the delivery duct (25); and d) in a neutral operating mode, the first valve (V1), the second valve (V2), the third valve (V3) and the fourth valve (V4) are all open to provide for the vacuum duct (34) to open to atmosphere by way of the fourth branch (39), the pressure duct (35) to be open to atmosphere by way of the first branch (36) and the sample chamber (20) to vent to atmosphere while the clamps (50, 51) are in an open position so that they do not inhibit the passage of liquid through the delivery duct (25); and 6) a prime mover (45) coupled to drive both the single and double lobed cams (46, 49) by way of the shaft (48) providing for operation of the first through fourth valves (V1, V2, V3, V4) and the delivery valve (25) to be mechanically related and be capable, while the compressor (32) is running, of transferring a sample from the body of liquid (10) to the collection device, said method comprising the steps of:

1) setting the valves to the first operating mode to purge air from the compressor (32) and any liquid from the sample inlet duct (22);
2) setting the valves to the second operating mode to draw liquid up the sample inlet duct (22) into the sample chamber (20) until the presence of the liquid at a desired level is detected by the liquid level sensor (L);
3) setting the valves to the third operating mode to allow the liquid in the sample chamber (20) above the inlet (22') to leave the sample chamber through the inlet sample duct (22) to return to the body of liquid (10); and
4) setting the valves to the neutral mode to allow the liquid in the sample chamber (20) below the inlet (22') to leave the sample chamber through the sample delivery duct (23) to a collection device (B').

* * * * *